United States Patent
Buttner et al.

(10) Patent No.: US 10,282,799 B2
(45) Date of Patent: May 7, 2019

(54) SIMPLIFIED SYSTEM FOR SHARING MEDICAL INFORMATION BETWEEN INSTITUTIONS

(75) Inventors: Mark D. Buttner, Verona, WI (US); Daniel J. Donoghue, Oregon, WI (US); David E. Fuhrmann, Verona, WI (US); Janet L. Campbell, Madison, WI (US); Brian M. Weisberger, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 1179 days.

(21) Appl. No.: 12/625,324

(22) Filed: Nov. 24, 2009

(65) Prior Publication Data

US 2010/0131298 A1 May 27, 2010

Related U.S. Application Data

(60) Provisional application No. 61/117,810, filed on Nov. 25, 2008.

(51) Int. Cl.
*G06Q 10/10* (2012.01)
*G06Q 50/22* (2018.01)
*G06Q 50/24* (2012.01)
*G16H 10/60* (2018.01)

(52) U.S. Cl.
CPC ............ *G06Q 50/22* (2013.01); *G06Q 10/10* (2013.01); *G06Q 50/24* (2013.01); *G16H 10/60* (2018.01)

(58) Field of Classification Search
CPC combination set(s) only.
See application file for complete search history.

(56) References Cited

U.S. PATENT DOCUMENTS

| | | | |
|---|---|---|---|
| 6,263,330 B1 * | 7/2001 | Bessette | |
| 6,476,833 B1 * | 11/2002 | Moshfeghi | 715/854 |
| 7,627,334 B2 * | 12/2009 | Cohen et al. | 455/456.3 |
| 7,680,865 B2 * | 3/2010 | Tashiro et al. | 707/784 |
| 2010/0328320 A1 * | 12/2010 | Kerstna et al. | 345/501 |

\* cited by examiner

*Primary Examiner* — Valerie Lubin
(74) *Attorney, Agent, or Firm* — Boyle Fredrickson, S.C.

(57) ABSTRACT

A computer-implemented system for transferring clinical medical data between healthcare institutions. The system includes a first electronic medical record system configured to maintain electronic medical records for a patient at a first healthcare institution and an integrated web browser configured to allow a patient at the first healthcare institution to connect to a web-based portal page of a second electronic medical record system at a second healthcare institution through the first electronic medical record system, wherein the web-based portal page is configured to provide information from the second electronic medical record system to be displayed through the integrated web browser. The system further includes a medical record parser configured to parse the displayed information for storage in the first electronic medical record system.

18 Claims, 2 Drawing Sheets

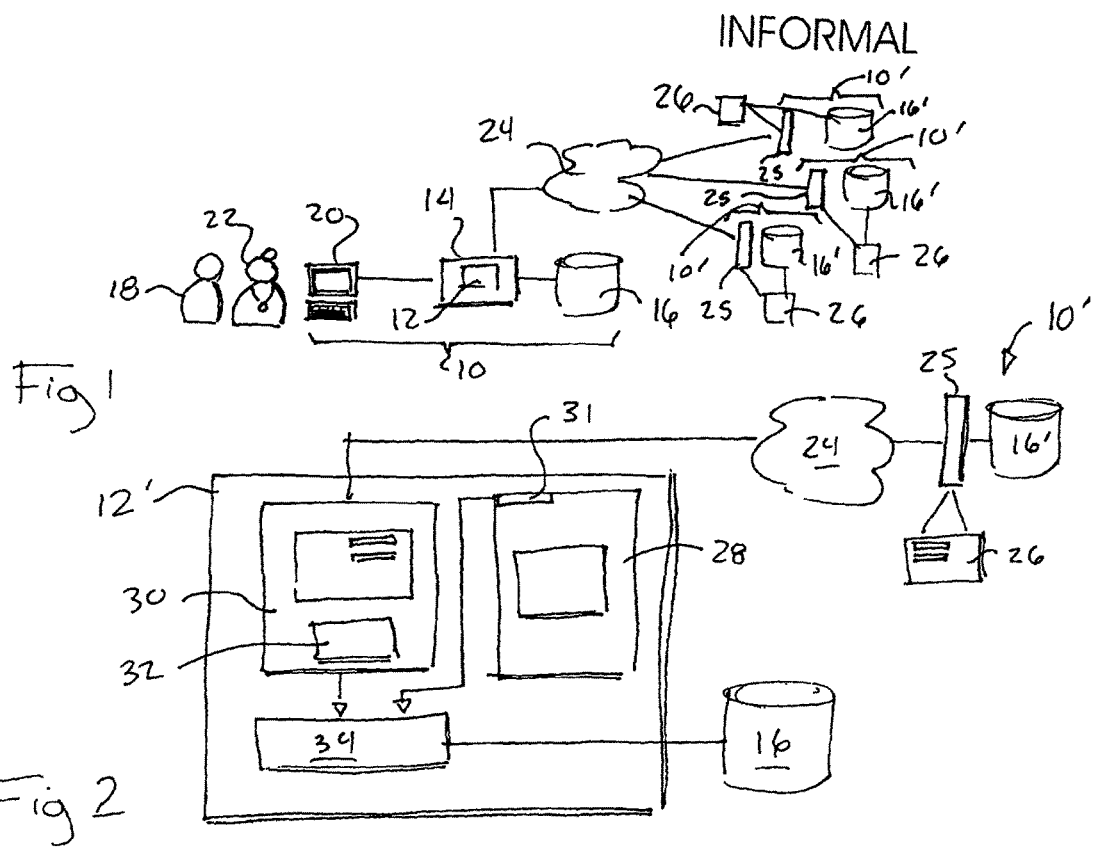
Fig 1
Fig 2
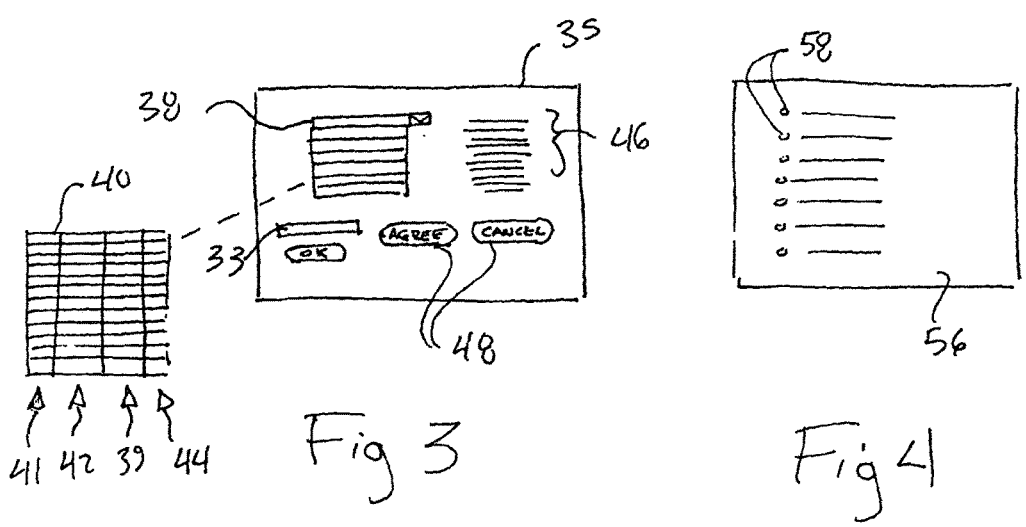
Fig 3
Fig 4

SIMPLIFIED SYSTEM FOR SHARING MEDICAL INFORMATION BETWEEN INSTITUTIONS

CROSS REFERENCE TO RELATED APPLICATION

This application claims the benefit of U.S. Provisional Application No. 61/117,810, filed Nov. 25, 2008, hereby incorporated by reference in its entirety.

BACKGROUND OF THE INVENTION

The present invention relates generally to electronic medical records and in particular to a system that simplifies the communication of electronic medical records among healthcare institutions involved in a patient's healthcare.

Electronic medical records are increasingly used in medical institutions such as clinics and hospitals as the primary source of clinical medical information for the treatment of patients. Such electronic medical records provide both a quickly accessible medical history of the patient and a convenient way for healthcare professionals to coordinate their efforts on the patient's behalf.

Ideally, electronic medical records could be made portable so as to provide continuity of care as a patient moves among institutions and electronic systems. Standard data formats for medical records, such as CCR and CCD, promote such portability by simplifying the import or export of data from a particular institution's medical record system. But these formats are not universally available or implemented, limiting their current impact on portability. Further, even with consistent data formats, the process of exporting data from one institution and importing it to another requires a substantial degree of preparation by the parties, including, for example, a request by a patient, identification of the appropriate records, preparation of required releases, transfer of the data, identifying corresponding files in the new record system, merging the imported data into the appropriate records, and notification to the patient. For this reason, a patient requiring healthcare on an urgent basis, in an unfamiliar venue, may not be able to rely on healthcare records at another institution regardless of their portability.

SUMMARY OF THE INVENTION

The present invention provides for impromptu sharing of electronic medical records by making use of a pre-existing web-based, e.g. web-accessible, portal page granted to the patient. A web-based portal page, such as MyChart offered by the Epic Systems Corporation of Verona, Wis., provides a patient with personal Internet access to his electronic medical record at a particular institution through the portal page. A portal page differs from a traditional personal health record (PHR) site in that the former provides electronic access to the patient's clinical medical records housed at a clinical organization, whereas the latter is principally a repository for patient-sourced medical information.

One embodiment of the present invention relates to a computer-implemented system for transferring clinical medical data between healthcare institutions. The system includes a first electronic medical record system configured to maintain electronic medical records for a patient at a first healthcare institution and an integrated web browser configured to allow a patient at the first healthcare institution to connect to a web-based portal page of a second electronic medical record system at a second healthcare institution through the first electronic medical record system, wherein the web-based portal page is configured to provide information from the second electronic medical record system to be displayed through the integrated web browser. The system further includes a medical record parser configured to parse the displayed information for storage in the first electronic medical record system.

In the present invention, the portal page may be used to allow the electronic medical records to be viewed by a healthcare provider using the aforementioned integrated web browser, the necessary permissions and passwords being provided by the physically present patient. No advanced preparation is required and the received data may be incorporated into the record currently open for the given care session. The nature of a portal page makes it likely that many patients will have access to such a site independent of an expectation of the need for transferring their medical data.

BRIEF DESCRIPTION OF THE DRAWINGS

FIG. 1 is a system diagram of an electronic medical record system at a first institution communicating over the Internet with portal pages associated with electronic medical record systems of other institutions;

FIG. 2 is a block diagram of the software components of the electronic medical record system of the present invention that may be used at the second institution and which provides an encapsulated browser system and data-importing program;

FIG. 3 is a screenshot of a screen generated by the web based portal page of the electronic medical record system of FIG. 2;

FIG. 4 is a file permission screen generated by the web based portal page of the electronic medical record system of FIG. 2.

DETAILED DESCRIPTION OF THE PREFERRED EMBODIMENT

Figure 5:
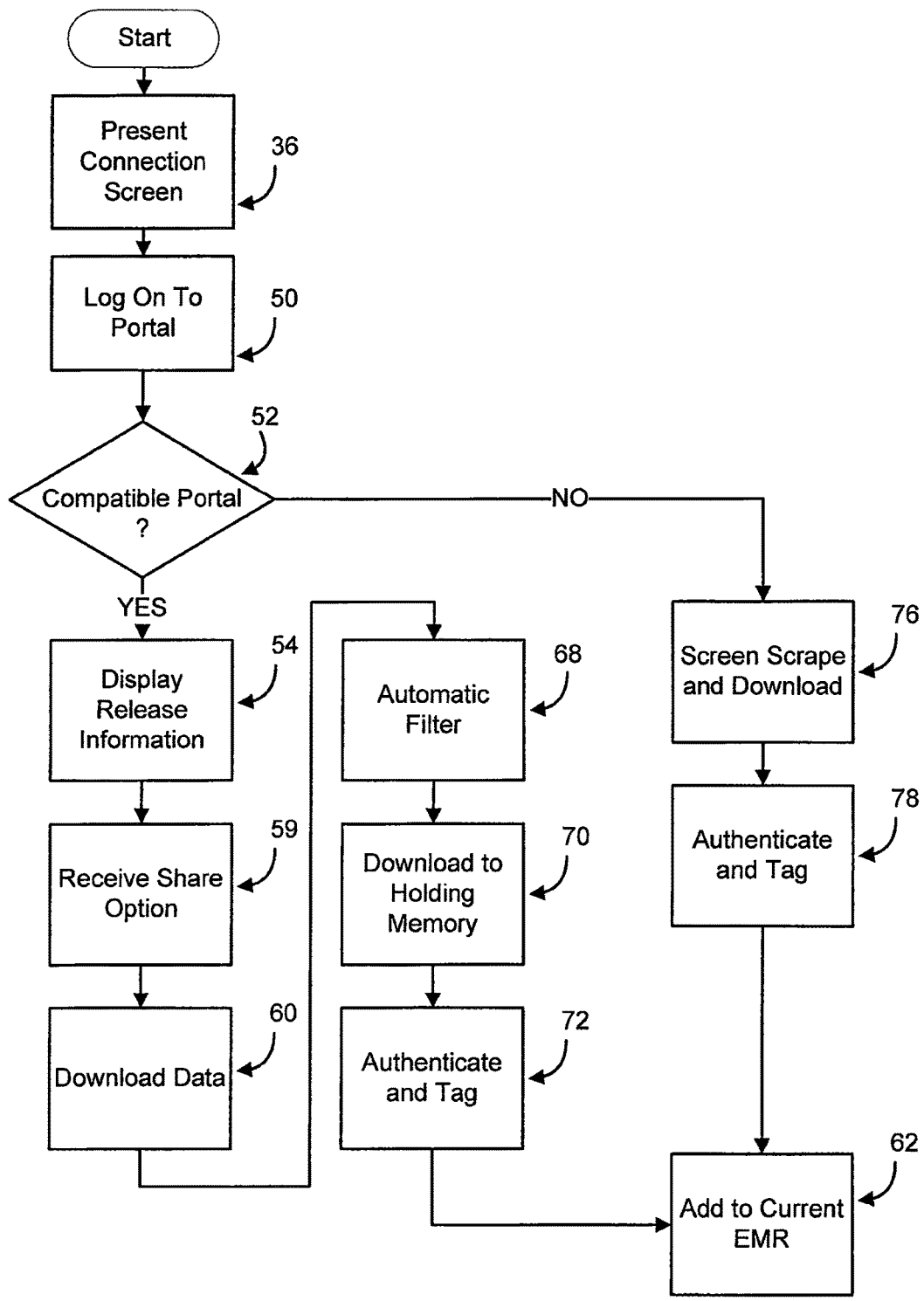
FIG. 5 is a flow chart of the importing program of FIG. 2.

Referring now to FIG. 1, the present invention may be integrated into an electronic medical record system (EMS) 10 at a first institution providing one or more computers 14 executing a stored augmented EMS program 12 as will be described. Generally, the EMS 10 may include or be associated with an electronic medical record (EMR) database 16 accessible by the augmented EMS program 12 and holding electronic medical records of a patient 18. "Electronic medical records" as used herein refers to medical records prepared, for example, by a physician or other healthcare provider, such as a nurse, a medical record keeper, etc., and which therefore can be relied on in a clinical environment.

The computers 14 and augmented EMS program 12 may support one or more terminals 20 available to healthcare providers 22 for access to electronic medical records in their daily practice.

The computers 14 may also provide for a connection to the Internet 24 and through the Internet 24 may access web-based portal pages 26 associated with electronic medical record systems 10' of other institutions. The portal pages 26 may generally be available through Web servers 25 and provide access to data from EMR databases 16' holding a patient's medical records for the other institutions.

The portal pages 26 may, for example, be implemented using the MyChart program described above which allows a patient 18 to access his or her electronic medical records over the Internet 24. Although described herein with reference to a patient, it should be understood that that a proxy, such as a parent, guardian, etc. entrusted with the patient's access information, may perform the steps described herein as being performed by the patient. As noted above, portal pages 26 should be distinguished from a personal health record (PHR) page which allows the storage of patient-sourced medical information but does not provide direct access by the patient 18 to his or her clinically-sourced medical records such as contained in EMR databases 16'. Because the portal pages 26 provide access to confidential information, typically such portal pages 26 implement a secure login procedure in which the patient 18 provides a user identification and a password or the like to ensure confidentiality of the released data.

The present invention makes use of portal pages 26, not simply to allow a patient access to his or her medical records, but to provide an impromptu method of transferring medical record data between institutions. This transfer of data, which does not require preplanning, may be useful for example when the patient is in an emergency situation in a remote healthcare institution or requires healthcare on a non-urgent basis but in a situation where a traditional transfer of health record information is impossible or impractical.

Referring now to FIGS. 1 and 2, the present invention provides an augmented EMS program 12 that includes a standard patient record component 28 and additional components 30 and 34 providing for the beneficial transfer of medical records described above. The standard patient record component 28, as understood in the prior art, operates with a local EMR database 16 to allow a healthcare provider 22 to view records of a current patient 18 identified by a patient record identifier 31. In addition, the standard patient record component 28 allows the healthcare provider 22 to add to or modify those records appropriately. The healthcare provider 22 may thus use the augmented EMS program like a paper file on the patient 18 to make diagnostic decisions and record a treatment history.

The additional components of the augmented EMS program 12 also include an integrated browser program 30 that works in the context of the augmented EMS program 12 like a standard browser to connect to the Internet 24, but that executes in a constrained manner. In particular, integrated browser program 30 operates with a memory file that is uniquely assigned to the particular patient record identifier 31 and that is purged when the records of the current patient 18 are closed. Further, the integrated browser program 30 may have limited browsing capabilities (operating with a whitelist of URLs) and high security features and may provide special clearance through a system firewall only for a limited set of URL addresses so as to provide heightened security. The integrated browser program 30 further may have limited ability to execute scripts or browser plug-in programs and constraints on the execution of those programs may be imposed beyond those normally provided in a browser.

During operation, the integrated browser program 30 presents a familiar browser screen on the terminal 20 in a manner to be visible to both the healthcare provider 22 and patient 18, typically present in the same room. The invention contemplates that the healthcare provider 22 will open the integrated browser program 30 so that the patient may use the browser and enter a web address to connect to his or her portal page 26. In this regard, the patient may make use of the keyboard and mouse of the terminal 20 to maneuver through a portal page 26 using the integrated browser program 30 in a manner similar to that done by the patient 18 on his or her home computer.

Referring now to FIGS. 1, 2, 3, and 5, in the present invention, the integrated browser program 30 works in conjunction with a data importing program 34 in the augmented EMS program 12 to present, upon opening of the browser, a start screen 35 as indicated by process block 36 and as shown in FIG. 3. Data importing program 34 may be any computer implemented system or method configured to download the selected data in a form that may be immediately integrated into the patient's EMR. The start screen 35 may simply be a standard browser screen allowing for the entry of a URL of a portal page 26 or may provide a menu structure 38 having a list of URLs of particular institutions and/or their portals. The menu structure 38 may be driven by an underlying table 40 linking names 41 of known official URLs 42 to eliminate the possibility of spoofing type data theft. Each URL 42 may also be linked to compatibility information 39 about the quality of the data and a data filter 44 which will also be described.

This start screen 35 may display the patient's identification information prominently at display box 33 which must be verified by the patient to ensure that the downloaded data matches the data of the patient associated with patient record identifier 31 of the currently open data record by the augmented EMS program 12. In this way, transferred data is assured of being transferred to the correct patient file. Optionally, the patient's identification information may also be verified by the attending healthcare provider 22.

The start screen 35 may have a release notice 46 advising the patient that he or she is releasing medical data to the given first institution and allowing agreement or cancellation buttons 48 or other electronic signature techniques. This release process is refined during the process to be described and will use a similar screen and electronic signature technique.

As indicated in FIG. 5 at process block 50, the patient 18 is presented with the standard start screen of the selected portal page 26 as interpreted by the integrated browser program 30, and a login using the patient's password or other identification information may be conducted according to the protocol of the particular portal page 26.

At decision block 52, the augmented EMS program 12 determines whether the portal page 26 indicated in the data table 40 is a "compatible" or "incompatible" portal page 26. A "compatible" portal page 26 will be one that can deliver data in an authenticated and standardized format allowing a high degree of integration with the patient's record in the augmented EMS program 12, and thus allowing for high-level sharing of electronic data about the patient 18. Compatible data will follow a standardized form of data expression both in the data context and the values of the data.

In the case where the portal page 26 provides compatible data, the augmented EMS program 12 proceeds to process block 54, and a "Release A" option augmenting that described with respect to FIG. 3, is provided indicating to the patient that a level of filtering control will be available and requesting permission for this data transfer.

If approved by the patient, the augmented EMS program 12 proceeds to process block 59 and the patient selects a "share" option implemented by the portal page 26. This share option displays a permission screen 56, implemented by the portal page 26, as shown in FIG. 4 providing checkmarks 58 that may be used to allow the patient 18 to select certain categories of information to share with the healthcare provider 22 using portal page 26 and which provides for an electronic signature or the like for such sharing through filter 44, implemented by the portal page 26. Only the checked categories of data will be transferred as indicated by process block 60 which initiates the data importing program 34 to download the selected data in a form that may be immediately integrated into the patient's EMR. The augmented EMS program 12 begins downloading at process box 70 to the sequestered memory 32 of the integrated browser program 30. The augmented EMS program 12 converts the standard format of the portal page 26 to a format compatible with the EMR database 16 of the augmented EMS program 12. The imported data is authenticated to the extent possible and tagged to the extent practical with an automatic tagging system at process box 72. The data is then added to the patient's EMR in EMR database 16 with the tags described above in a step 62. The tags may generally indicate source of the data, the time of transfer of the data, and whether the data is patient-sourced or clinical data as well as categories and meaning of the data. The present invention contemplates that this situation will be common and will provide a benefit of the present invention. Significantly, this integration process may make use of the patient record identifier 31 associated with an open patient file thus assuring the correct data is transferred to the correct data file. The data from a compatible portal page 26 may include, for example, watermarking or other security features to allow the healthcare provider 22 to have a high degree of certainty that the data is collected by other healthcare professionals. The data may be tagged indicating its source from the institution and the form of transfer from a compatible system. Optionally, patient-sourced data may also be downloaded and indicated as such when integrated into the patient's electronic medical record database.

Referring still to FIG. 5, if at decision block 52 the portal page 26 is determined is "incompatible" per table 40, the patient 18 may be presented with a "Release B" indicating that all data on display screens will be subject to release. The patient 18 may then select particular screens displaying medical records and, by activating a capture button superimposed over a toolbar surrounding the browser window, may capture those screens. These images may be "scraped" as indicated by process block 76 by looking at the underlying source of an HTML screen for text and interpreting that text, or the image submitted to optical character recognition, or simply captured as an image or HTML file and stored. In all cases, the data is tagged coarsely (as to source and time) as indicated by process box 78 and incorporated into the patient's EMR database 16 in the step 62 as described above.

The present invention takes advantage of a pre-existing Internet interface available through portal page 26 to provide a path for unplanned data transfer to an attending healthcare provider 22 in cases where it would be helpful for the healthcare provider 22 to have access to data from another institution, but where a formal data connection between institutions has not been obtained.

According to an exemplary embodiment, portal page 26 may further be configurable such that the healthcare provider 22 may upload new medical record information, generated based on the visit to the first institution, to the electronic medical record systems 10' of other institutions. Advantageously, this feature can be used to maintain continuity of the electronic medical record systems 10' at the other institutions. This feature may be useful, for example, where a patient visits a healthcare provider while travelling and wants the visit and its conclusion to be reflected in their electronic medical record system 10' at their home institution.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. A computer-implemented system for transferring clinical medical data between healthcare institutions, comprising:
a first electronic medical record system configured to maintain electronic medical records for a patient at a first healthcare institution, the system including a user interface receiving user identification and authentication information to identify a user as a patient and log the user into the electronic medical record of the patient allowing the user to select medical record information for display in the user interface;
an interactive web browser integrated into the user interface such that it can only be launched from within the user interface after successfully logging into the electronic medical record of the patient in the first electronic medical record system, the interactive web browser configured to receive a web-based portal page selection from a patient after the interactive web browser has been launched, where the portal selection allows the patient at the first healthcare institution to connect to a web-based portal page of a second electronic medical record system at a second healthcare institution and select medical record information from a second electronic medical record of the patient at the second healthcare institution for display in the interactive web browser, the functionality of the interactive web browser being constrained based on information in the first electronic medical record, wherein the web-based portal page is configured to provide medical record information from the second electronic medical record of the patient from the second electronic medical record system to be displayed through the integrated interactive web browser; and
a medical record parser configured to parse the displayed information for storage in the first electronic medical record system.

2. The system of claim 1, wherein the browser operates in a constrained memory space associated with the patient that is purged when the records of the patient in the first electronic medical record system are closed.

3. The system of claim 2, wherein the browser operates from a whitelist of URLs limited to web-based portal pages.

4. The system of claim 1, wherein the web-based portal page is configured to provide a selection interface allowing the patient to select one or more sections of the information from a second electronic medical record system's record to be provided.

5. The system of claim 1, wherein the web browser is an Internet browser.

6. The system of claim 1, wherein the first electronic medical record system is configured to determine whether the patient has authorization to view and transfer information from the second electronic medical record system.

7. The system of claim 6, wherein the authorization is based on relationship information stored at the second electronic medical record system.

8. The system of claim 1, wherein the web browser is configured to provide information entered into the first electronic medical record system to the second electronic medical record system.

9. The system of claim 1, wherein parsing the displayed information includes converting the information from an extensible markup language.

10. The system of claim 1, wherein parsing the displayed information includes providing one or more screenshots of the displayed information.

11. A computer-implemented method for transferring clinical medical data between healthcare institutions, comprising:
receiving user identification and authentication information at a first electronic medical record system on a first computer system to identify a user as a patient and log the user into an electronic medical record of the patient allowing the user to select medical record information for display in the user interface;
displaying an interactive web browser integrated into the user interface such that it can only be launched from within the user interface of the first electronic medical record system after successfully logging into the electronic medical record in the first electronic medical record system on the first computer system,
receiving a web-based portal page selection from a patient after the interactive web browser has been launched,
connecting to a web-based portal page of a second electronic medical record system at a second healthcare institution on a second computer system,
receiving a selection of medical record information from a second electronic medical record of the patient at the second healthcare institution for display in the interactive web browser,
wherein the functionality of the interactive web browser is constrained based on information in the first electronic medical record,
further wherein the web-based portal page is configured to provide medical record information from the second electronic medical record of the patient from the second electronic medical record system to be displayed through the interactive web browser;
parsing the provided information for storage in the first electronic medical record system on the first computer system; and
storing the parsed information in the first electronic medical record system.

12. The method of claim 11, wherein the web-based portal page is configured to provide a selection interface allowing the patient to select one or more sections of the information from a second electronic medical record system's record to be provided.

13. The method of claim 11, wherein the web browser is an Internet browser.

14. The method of claim 11, further including determining whether the patient has authorization to view and transfer information from the second electronic medical record system prior to displaying the information.

15. The method of claim 14, wherein the authorization is based on relationship information stored at the second electronic medical record system.

16. The method of claim 11, further including providing information entered into the first electronic medical record system to the second electronic medical record system.

17. The method of claim 11, wherein parsing the displayed information includes converting the information from an extensible markup language.

18. The method of claim 11, wherein parsing the displayed information includes capturing one or more screenshots of the displayed information.

* * * * *